United States Patent
Greff

(10) Patent No.: US 6,372,717 B1
(45) Date of Patent: Apr. 16, 2002

(54) SYNTHETIC PEPTIDES AND THEIR USE IN COSMETIC OR DERMOPHARMACEUTICAL COMPOSITIONS

(75) Inventor: Daniel Greff, Mere (FR)

(73) Assignee: Sederma S.A., Le Perray-en-Yvelines (FR)

( * ) Notice: Subject to any disclaimer, the term of this patent is extended or adjusted under 35 U.S.C. 154(b) by 0 days.

(21) Appl. No.: 09/242,687

(22) PCT Filed: Aug. 23, 1996

(86) PCT No.: PCT/FR96/01322

§ 371 Date: Feb. 23, 1999

§ 102(e) Date: Feb. 23, 1999

(87) PCT Pub. No.: WO98/07744

PCT Pub. Date: Feb. 26, 1998

(51) Int. Cl.$^7$ ............ A61K 38/00; C07K 7/00; G01N 33/00

(52) U.S. Cl. ............ 514/19; 514/18; 514/887; 514/928; 530/333; 530/335; 530/337; 530/343; 530/345; 436/85; 436/86; 436/89

(58) Field of Search .................. 514/19, 18, 887, 514/928; 530/333, 335, 337, 343, 345; 436/85, 86, 89

(56) References Cited

U.S. PATENT DOCUMENTS 4,489,062 A * 12/1984 Lowe et al. ............... 424/177
4,540,682 A * 9/1985 Hardy et al. ............... 514/18

FOREIGN PATENT DOCUMENTS

WO    WO 94/09750    * 5/1994

OTHER PUBLICATIONS

Fidler, *Eur. J. Biochem.*, vol. 163, pp. 303–312, 1987.*

Kaschet et al., *Biotechnology and Bioengineering*, vol. 45, pp. 261–267, 1995.*

* cited by examiner

Primary Examiner—Christopher S. F. Low
Assistant Examiner—Abdel A. Mohamed
(74) Attorney, Agent, or Firm—Young & Thompson

(57) ABSTRACT

The invention concerns the use of peptides of general formula R1-L-Tyr-L-Arg-R2 in which R1=H or a R3-C=0 with R3=a C1 to C20 alkyl chain, linear or branched, saturated or unsaturate, hydroxylated or not, or with R3=an aryl, aryl-alkyl or alkyloxy or aryloxy or arylalkyloxy group, and in which R2=OH or a O-R4 group with R4=a C1 to C20 alkyl chain, or R2=a NH2, NHX or NXX group with X=a C1 to C4 alkyl chain. The peptides have a soothing effect on the skin, including by topical application, and attenuates the effects of benign skin sores (after shave irritation, sunstroke, frostbite, chaps, depilation). They are used in acceptable cosmetic excipients and in effective in vivo concentrations.

10 Claims, No Drawings

SYNTHETIC PEPTIDES AND THEIR USE IN COSMETIC OR DERMOPHARMACEUTICAL COMPOSITIONS

The skin is the largest organ of the body, but also the most exposed to various sources of harm: irritation due to the environment (pollution, allergies), to the weather (wind, rain, cold, solar radiation, drying), to physical treatments (shaving, epilation, abrasions, shocks). Whilst being a protective member of the whole organism against dehydration, against bacterial or molecular invasion, the skin serves also to communicate with the environment and to register sensations of touch. It is therefore completely provided with nerves, the sensations of pain or discomfort or quite localized in the epidermis of the entire body.

Anatomical, histological and physiological analyses have shown cells connected to the nervous system which could be the cells responsible, at least partially, for the transmission of the sensations of touch, and above all of pain. These cells are called "Merkel cells".

Recent studies have shown by immunoreactivity, the presence of a certain number of neuropeptides at the level of the epidermis, adjacent the Merkel cells. Among these neuropeptides are enkephaline, a peptide of the sequence Tyr-Gly-Gly-Phe-Leu(Seq ID No:1), whose activity known at present is suppression of pain (analgesic effect) by action on the receptor of morphine in the brain. This peptide has been discovered, apart from cerebral tissue, in other places in the body, at the periphery, and hence also in the skin. Its role is not yet known. Other studies have shown that the release of the peptide in the brain, upon an inherent need with an analgesic effect, takes place by means of another peptide of the sequence Tyr-Arg. This peptide is not connected to the morphine receptor itself, but it induces the synthesis or the release of enkephaline and thereby provokes a rapid—but fleeting—suppression of pain. This peptide has until now only been found in the brain, and its activity has not been described other than by direct intracerebral administration.

The object of the present invention is the discovery that this peptide, and above all the lipophile derivatives of the peptide, have a calming, antalgic activity when applied to the human skin in a suitable cosmetic or dermopharmaceutical preparation.

The peptides correspond to the general formula: R1-L-Tyr-L-Arg-R2 in which R1=a group R3-C=O wherein R3 is an alkyl chain of C1 to C20, linear or branched, saturated or unsaturated, hydroxylated or not, or with R3=an aryl, arylalkyl, or alkyloxy, group, and in which R2=a group O-R4 wherein R4 is an alkyl chain of C1 to C20, or R2 equals an NH2 or NHX or NXX group wherein X is an alkyl chain of C1 to C4.

The non-lipophilic peptide H-L-Tyr-L-Arg-OH has only a slight activity by topical application, because it penetrates through the corneal layer only with difficulty. The modification which consists in attaching by an amide linkage a fatty chain (alkyl) or an aromatic residue (aryl) or their alkyloxy or aryloxy or arylalkyloxy variants on the NH of tyrosine, and/or attaching by ester linkage a fatty alcohol (alkyl) or by amide linkage a group NH2 or NHX or NXX wherein X=an alkyl chain of C1 to C4, confers on the peptide a substantially greater affinity for the skin and an increased power of penetration which increases very greatly the biological activity of the peptide.

The peptide can be obtained by conventional peptidic syntheses or by enzymatic route.

By way of example, arginine can be esterified with a short chain alcohol (butyl) by acid condensation, then Boc-tyrosine is attached to the ester of arginine by the conventional method of activated ester (ethyl chloroformate or DCC), then palmitic acid is attached by the acid chloride method to obtain N-palmitoyl-L-Tyr-L-Arg-O-butyl. The synthesis by enzymatic route uses enzymes of the chymotrypsin or trypsin type in a preferably anhydrous medium to couple the aminated acids Tyrosine and Arginine, then the tyrosine is acylated to obtain N-acyl-L-Tyr-L-Arg.

Those skilled in the art of peptide synthesis know how to prepare derivatives of the general formula indicated by the known methods.

The peptides and its derivatives, which are the objects of the present application, must be carried in a suitable cosmetic or dermopharmaceutical preparation. According to the nature of the residues R1 and R2 and X, it can have variable solubility. The preferred embodiment of the invention is constituted by peptides of the nature N-acyl$^A$-L-Tyr-L-Arg-O-alkyl$^B$, wherein acyl$^A$ is an alkyl chain of C1 to C18, preferably C1 to C4, and alkyl$^B$ is an alkyl chain of C1 to C18, preferably C8 to C16. A particularly preferred embodiment is constituted by the peptide N-Acetyl-L-Tyr-L-Arg-O-hexadecyl. It is obtained by synthesis in the following way:

300 ml of toluene is heated 100° C., then there is added 20 g of hexadecanol and 34 g of PTSA (paratoluene sulfonic acid), then there is gradually added 17 g of L-Arginine.HCl. A sterification is effected by refluxing overnight. Precipitation is effected with TEA, followed by filtration and drying of the precipitate (hexadecyl ether of L-arginine). Then 5.6 g of N-acetyl-L-tyrosine is prepared in 75 ml of THF, to which is added 3 g of N-hydroxysuccinimide in 20 ml of THF. There is added a solution of 5.3 g DCC (Dicyclohexylcarbodiimide) in 20 ml of dichloromethane. After quantitative formation of DCU and filtration, there is added a solution of the ester of L-Arginine in THF (14 g in 200 ml of THF) and this is allowed to react for 48 hours at ambient temperature. The solvent is evaporated and it is crystallized in water, then filtered and dried. The obtained product (18 g) is characterized by thin layer chromatography, HPLC, infrared and melting point (140–143° C.).

These peptides are generally not soluble in water, but can be dissolved in conventional cosmetic or dermopharmaceutical solvents such as ethanol, propanol or isopropanol, propylene glycol, glycerin, butylene glycol, ethoxydiglycol, polyethylene glycol, methyl or ethyl ethers of diglycols, cyclic polyols, ethoxylated or propoxylated glycols or any mixture of these solvents. Those skilled in the art know methods of preliminary solubilization of this type of molecule. The peptides can also be previously incorporated in cosmetic vectors such as liposomes, chylomicrons, macro-, micro- and nanoparticles as well as macro-, micro- and nanocapsules, or be adsorbed on powdered organic polymers, talcs, bentonites and other mineral supports. These solutions or preparations can then be used in creams, lotions, pomades or other cosmetic and dermopharmaceutical preparations.

By way of example, can be cited as preparation of a peptide representative of the invention:

Example No. 1:

| | |
|---|---|
| 1,3 Butylene glycol | 40% |
| Tween$^R$ 20 | 1% |
| Ethoxydiglycol | 35% |

-continued

| | |
|---|---|
| Propylene glycol | 22% |
| N-Acetyl-L-Tyr-L-Arg-O-Hexadecyule | 2%. |

Example No. 2:

| | |
|---|---|
| Water | 20% |
| Ethanol | 30% |
| Isopropanol | 30% |
| Glycerine | 17% |
| N-Propyl-L-Tyr-L-Arg-O-Octadecyl | 3%. |

Example No. 3:

| | | |
|---|---|---|
| Solution of the peptide incorporated in a cream of the emollient type: | | |
| BRIJ 721 (polyoxyethylene ether nonionic detergent) | | 2.4 |
| BRIJ 72 (polyoxyethylene ether nonionic detergent) | | 2.6 |
| ARLAMOL E (polar emollient for creams and lotions) | | 8.0 |
| Beeswax | | 0.5 |
| ABIL ZP 2434 (stearly dimethicone emollient) | | 3.0 |
| Propylene glycol | | 3.0 |
| CARBOPOL 941 (carbomer emulsion stabilizer) | | 0.25 |
| Triethanolamine | | 0.25 |
| Solution of the peptide of Example No. 1 | | 5.0 |
| Water, preservatives, perfumes | qsp | 100 g. |

The cosmetic or dermopharmaceutical effects of the peptides which are the objects of the invention have been determined by in vivo tests:

The peptides which are the object of the present invention can be used in any galenic form conventionally used in cosmetic or dermopharmaceutical formulations: oil/water and water/oil emulsions, milks, lotions, gels, pomades, balms, foams, body oils, capillary lotions, shampoos, soaps, sticks and pencils, sprays, this list being not limitative.

The concentration of use of these peptides in the final cosmetic product can vary between 0.001 and 10% (p/p), preferably between 0.01 and 1% by weight of the total compositions.

The peptides which are the object of the present invention can be combined in cosmetic compositions with any other ingredient conventionally used in cosmetology: extracted and/or synthesized lipids, gelling and thickening polymers, surface active agents and emulsifiers, hydrosoluble or liposoluble active principles, plant extracts, tissue extracts, marine extracts. The peptides in all their galenic forms (powder, solution, emulsion) can be used in cosmetic and dermopharmaceutical fields for their tranquilizing and analgic activity. They are preferably used in products for sensitive skin, sun cream and after sun, after shave lotions, depilatory creams or after depilation creams, without this list being exhaustive. Their use is thus appropriate for all needs of the skin or scalp, particularly relief of sensations of irritation, mild pain, effects of heat, cold, abrasion or mechanical attack on the skin.

SEQUENCE LISTING

```
<160> NUMBER OF SEQ ID NOS: 1

<210> SEQ ID NO 1
<211> LENGTH: 5
<212> TYPE: PRT
<213> ORGANISM: Homo sapiens

<400> SEQUENCE: 1

Tyr Gly Gly Phe Leu
 1               5
```

Example No. 4

Twenty volunteers were selected for this test. There was applied to each of these persons a heating probe with an integrated thermometer which permits heating a small region of the skin and measuring its temperature. The persons indicate, at different intervals, the passage beyond predefined thresholds of "warm", "hot", "very strongly hot" and "pain". After having learned these standards and their own sensation thresholds, the persons apply the cream containing the peptide to be tested, to the skin, on a measurement region. After variable delays (between 15 minutes and 4 hours), the thresholds of sensitivity to heat are again determined in the same way. It is thus possible to measure a possible decrease in sensitivity (emollient or antalgic effect), by comparison with a placebo containing no peptide. An index of emollient effect is computed by heat level.

The effectiveness of the peptides which are the object of the present invention is demonstrated in this test: the decrease of sensitivity to heat is noticeable after 30 minutes and significant after 2 hours. The index of emollient effect increases by 62% at 30 minutes, by 210% after 2 hours and by 80% after 4 hours.

What is claimed is:

1. Synthetic peptides for cosmetic or dermopharmaceutical topical administration, consisting of the formula: R1-L-Tyr-L-Arg-R2, wherein R1 is an R3-C=0 group, R3 is an alkyl chain of C1 to C20, linear or branched, saturated or unsaturated, hydroxylated or not, or wherein R3 is an aryl, aryl-alkyl or alkyloxy group, and wherein R2 is a group O-R4 wherein R4 is an alkyl chain of C1 to C20, or R2 is an NH2 or NHX or NXX group wherein X is an alkyl chain of C1 to C4.

2. Synthetic peptides according to claim 1 wherein the peptides are obtained either by peptidic synthesis in homogeneous or heterogeneous medium, or by enzymatic synthesis in an anhydrous medium.

3. Synthetic peptides according to claim 1 wherein when R3 is an aliphatic chain of C1 to C20 and R2 is O-R4 and R4 is a linear saturated or unsaturated C1 to C20 chain, each of R2 and R4 is C1–C18.

4. Synthetic peptides according to claim 1 wherein the peptide is N-Acetyl-L-Tyr-L-Arg-O-hexadecyl.

5. Cosmetic or dermopharmaceutical compositions containing at least one peptide according to claim 1 incorporated in cosmetic vectors selected from the group consisting liposomes, chylomicrons, macro-particles, micro-particles, nanoparticles, macro-capsules, micro-capsules and nano-capsules; or adsorbed on powdered organic polymers, talcs, bentonites or other mineral supports.

6. A method of relieving sensations of irritation, mild pain, effects of heat, cold, abrasion or mechanical attacks on the skin, comprising applying topically an effective amount of a composition according to claim 5.

7. Cosmetic or dermopharmaceutical compositions containing at least one peptide according to claim 1, solubilized in a solvent selected from the group consisting of water, ethanol, propynol, isopropynol, propylene glycol, butylene glycol, glycerin, polyethylene glycol, ethoxdiglycol, methyl and ethyl ethers of diglycols, cyclic polyols, ethoxylated and propoxylated diglycols and mixtures of these solvents.

8. Cosmetic or dermopharmaceutical compositions according to claim 7 containing peptides at concentrations between 0.001% and 10% by weight of the total composition.

9. Cosmetic or dermopharmaceutical compositions according to claim 7 having a galenic form employed in cosmetology or dermopharmacy, and selected from the group consisting of oil in water emulsions, water in oil emulsions, milks, lotions, gels, pomades, balms, foams, body oils, capillary lotions, shampoos, soaps, sticks, pencils and sprays.

10. Cosmetic or dermopharmaceutical compositions according to claim 7 wherein the peptides are combined in final products with lipids, gelling and thickening polymers, surface active agents, emulsifiers, hydrosoluble or liposoluble active principals, plant extracts, tissue extracts, or marine extracts.

* * * * *